United States Patent [19]
Gorinsky

[11] Patent Number: 5,786,385
[45] Date of Patent: Jul. 28, 1998

[54] POLYACETYLENES

[76] Inventor: Conrad Gorinsky, The Old House, Old House Lane, Nazeing, England, EN92LT

[21] Appl. No.: 644,894

[22] Filed: May 10, 1996

Related U.S. Application Data

[63] Continuation-in-part of Ser. No. 434,116, May 2, 1995, abandoned, which is a continuation of Ser. No. 189,681, Feb. 1, 1994, abandoned.

[30] Foreign Application Priority Data

Feb. 1, 1993 [GB] United Kingdom ............... 9301920

[51] Int. Cl.⁶ .................... A61K 31/40; C07D 315/00
[52] U.S. Cl. .................... 514/460; 549/416; 549/420
[58] Field of Search .................... 514/460; 549/416, 549/420

[56] References Cited

PUBLICATIONS

Chemische Berichte, vol. 108, No. 2, 1975, Weinheim De pp. 437–439 F. Bohlmann "ein Neues Sesquiterpenlacton aus Matricaria suffructicosa Var. Leptoloba".

Chemische Berichte vol. 107, No. 2, 1974, Weinheim De pp. 654–656 Bohlmann "Synthese Des Ichthiotherol–Acetats".

Chemical Abstracts, vol. 97, No. 11, 1982, Abstract No. 3501c Bohlmann et al "Naturally Occuring Terpene Derivatives. Part 379"p. 355 col. 1.

Chemical Abstracts, vol. 80, No. 11, 1974, abstract No. 12513j, Gorinsky et al "Isolation of Ichthiothereol and its Acatate from Clibadium Sylvestre" p. 223. col. 1.

*Primary Examiner*—Floyd D. Higel
*Attorney, Agent, or Firm*—Nixon & Vanderhye

[57] ABSTRACT

A 2-(1-nonen-3,5,7-triynyl)3-hydroxy tetrahydropyran (cunaniol) particularly that having the formula:

or a corresponding anhydrocunaniol or cunanione, for use in therapy, especially as a reversible heart blocking agent or neuromuscular active or in neurofunction generally; or for use as a pesticide or mycobactericide.

6 Claims, No Drawings

POLYACETYLENES

This application is a continuation-in-part of application of Ser. No. 08/434,116 filed 2 May 1995, now abandoned, which is a continuation of application Ser. No. 08/189,682, filed 1 Feb. 1994, now abandoned.

The invention relates to polyacetylene derivatives, and especially to the tetrahydro pyranol derivatives known as cunaniols, and their derivatives.

The term "cunani" has long been used by Amerindians for a group of fast acting fish poisons. Such fish poisons are generally derived from plants, and especially from the leaves thereof. South America probably possesses greater numbers of recorded fish poison plants than any other continent. For example, Guyana is thought to have about 40 such fish poison plants.

Effective fish poisons may be derived from the root of the Kurukuruwai plant, or from the sap, leaves or stems of the Kumarau plant. The fruit of the Sisal plant may be crushed in water and used as a fish poison.

The present invention however is concerned with a particular class of compounds which are polyacetylenes as set out in the claims herein, and their derivatives. These polyacetylenes include cunaniols of the following general formula I:

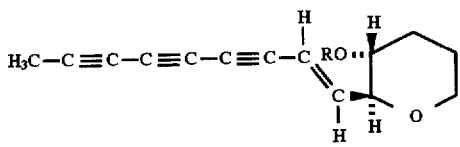

wherein R is H, alkyl (especially methyl), acyl or glycosidyl. The invention further embraces the corresponding anhydrocunaniols and cunanione and derivatives arising by hydrogenation of the hydrocarbon chain.

The structures of the anhydrocunaniols correspond to the dehydration products of cunaniol (R=H) above i.e. removal of the OH group at the 3-position of the ring together with the removal of a hydrogen atom at either adjacent carbon. These structures are shown as formulae II and III below.

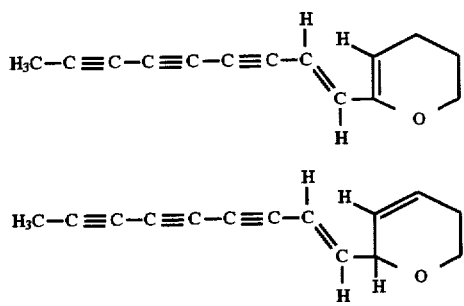

The structure of cunanione corresponds to the removal of the RO and H groups of formula I above to give a carbonyl group at the 3-position of the ring, as shown in formula IV below.

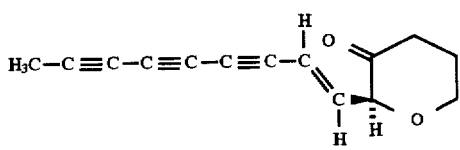

The synthesis of the anhydrocunaniols and cunanione from cunaniol can, of course, be readily achieved using standard chemical procedures known to those skilled in the art.

The above compounds may be isolated from leaves of the plant *Clibadium sylvestre* (Aubl.) Baill., which is a member of the family Compositae, trans cunaniol being the most abundant. It has long been recognised that the crushed leaves of this plant in water cause fish to surface and jump out of the water. Death results from the poison following paralysis. Gill action appears to be maintained to the end. Cunani is used as a general fish poison, but is also mixed with some starch and made into small balls which are fed to fish, which become disorientated on eating it and are easily caught by hand.

In the isolation of cunaniols, extracts of leaves from *Clibadium sylvestre* (Aubl.) Baill. may be prepared using refluxed petroleum 60/180, or in a cold extraction process with petrol 60/80, or in a mass extraction process using ethanol. The extract of cunani leaves may be further refined using a Quickfit and Quartz (Stone, Staffordshire, UK) steady state counter current distribution machine (SSDM). The lower phase fractions from the SSDM may then be collected and concentrated. This extract may then be further purified, for example, by column chromatography, to obtain cunaniol acetate.

The lower phase concentrate from the SSDM may be extracted e.g. with n-hexane, and submitted to column chromatography to obtain trans-cunaniol.

Cunaniol acetate can be isolated directly from the leaves of the cunani plant, or cunaniol can be derivatised to provide cunaniol acetate. The anhydrocunaniol and cunanione can also be isolated from the leaves of the cunani plant.

As noted above the invention embraces derivatives of cunaniol, such as the alkyl, acyl or glycosidyl derivatives. Examples of suitable derivatives include derivatives of essential fatty acids such as gamma-linolenic acid or dihomo-gamma-linolenic acid or others of the twelve n-6 and n-3 essential fatty acids, which are novel compounds and an aspect of the invention in themselves whether based on the fatty acids as such or in the corresponding fatty alcohols.

Hydrogenation where desired is carried out by standard catalytic hydrogenation methods to give fully or partly hydrogenated derivatives.

The cunaniol molecule and its related molecules are lipophilic, due to the presence of the polyacetylene chain. The molecules can therefore perturb cell membrane function. Crude extracts of the cunani plant are known to be very effective and extremely quick-acting fish poisons, the active agent in the cunani fish poison being cunaniol or its derivatives.

PHYSIOLOGICAL PROPERTIES

CNS Stimulant

Cunaniol is about ten times as active and ten times as rapid as the classic central nervous system stimulant picrotoxin. Convulsant action can be antagonised by prior exposure to anticonvulsants such as phenobarbitone or troxidone. In structure-activity relationship studies it was found that the highly unsaturated side chain was essential for convulsant activity. When administered to frogs by injection or by topical application cunaniol causes clonic convulsions and death (intraperitoneal injection LD50 is 12.8 mg/kg). The effects of cunaniol on frog spinal cord preparation resemble those of nicotine.

Cunaniol has been shown to be a clonic convulsant when administered intraperitoneally or orally into mice. The convulsant actions of cunaniol were mimicked closely by leptazol, and less closely by picrotoxin, but differed from the tonic convulsions produced by strychnine. Cunaniol was the most potent of the clonic convulsants by both routes of administration, and its effects usually occurred more rapidly than with the other compounds. In comparison, rotenone (a metabolic toxin) for example, was highly toxic to mice but its effects were qualitatively different from the convulsants. Rats are also sensitive to the convulsant actions of cunaniol, a convulsant dose being 5 mg/kg. A dosage of 2.24 mg/kg is a non-convulsant dose while 10 mg/kg causes death (intraperitoneal injection).

The effects of cunaniol on pentobarbitone sodium induced sleep in rats were compared with those of the analeptic bemegride. 5 mg/kg of cunaniol administered by intraperitoneal injection antagonises pentobarbitone while 7.4 mg/kg reduces "sleeping time" by 50% after intraperitoneal administration of a concentration of 40 mg/kg pentobarbitone sodium. In this respect cunaniol proved more potent than bemegride (45.7 mg/kg for a 50% reduction of "sleeping time").

Thus, cunaniol demonstrates advantages over bemegride and leptazol as an analeptic and may prove to be of value as an antagonist in the treatment of barbiturate-induced central depression and suggests a more selective anti-phenobarbitone action.

Cunaniol is a GABA (gamma-amino-butyric acid) antagonist, and thus an important probe for the GABAergic system.

Cardiac Properties and other effects on the Cardiovascular System

Cunaniol exhibits a dual action on the cardiovascular system, comprising a transient depressant effect on the heart and a sustained pressor response, probably centrally mediated.

Preliminary experiments on the isolated rabbit heart demonstrated that perfusion with high cunaniol concentrations (100 µg/ml) results in a negative inotropic effect culminating in complete but reversible cardiac arrest in diastole. A similar experiment with rotenone did not exhibit the reversibility.

Small doses of cunaniol reduce contractability of the rat heart, whereas larger doses cause complete heart block. This is rapidly reversed on washing out and with no apparent impairment of function.

In intact anaesthetised rats, a sustained pressor response is produced by cunaniol administered by intravenous injection in doses of 0.5 mg or greater. In pithed rats the response to cunaniol was abolished, indicating a central action of the polyacetylene.

Neuro-Muscular Action

Experiments have been carried out on frog and rat isolated striated muscle preparations. It was found that cunaniol causes an increased response to nerve stimulation, followed at higher concentrations by a failure in neuromuscular transmission.

The effects of cunaniol on the isolated rat phrenic nerve-diaphragm preparation are characterised by a marked potentiation by direct action on the muscle at concentrations as low as 12.5 µg/ml, this effect being dose dependent, followed by complete neuromuscular block at higher concentrations (100 µg/ml). This is not reversed by neostigmine, i.e. is not curare-like. The block is readily reversed by washing but the potentiation is more slowly (60 mins) removed.

APPLICATIONS

Applications may therefore include use as a rapidly reversible local anaesthetic or as a cardiac membrane stabiliser, and generally as a reversible heart blocking or heart recovery agent or as a neuromuscular active (i.e. a drug that acts on myoneural junctions) or as a neuroactive in neurofunction broadly (i.e. as a drug that has activity and provides benefits in conditions that affect neurofunction). As stated above, cunaniol may also be of use as an analeptic. Other applications may include use as a muscle stimulant. The lipophilic nature of the compounds enables them to pass the blood-brain barrier, an effect enhanced by essential fatty acid derivatisation.

Furthermore, the neurotoxic properties may be made use of in pesticides against insects or any other pest having vulnerable neurofunction, by application to the pest or to a substrate affected by or to be protected from the pest. The structure of the compounds also indicates use as a mycobactericide, mycomycin being a tri-yne mono-ene antibiotic.

Cunaniol or its derivatives may also be used as an effective toxin. When tested on guppies at approximately $10^{-6}$M the poison gives rise to restless movement after two minutes, wild swimming, convulsion and coma with the body bent laterally after ten minutes. If the fish are removed into fresh water at this stage, they recover completely in approximately twenty minutes and show no subsequent symptoms. Fish treated in this way are found to be edible almost immediately. Phenobarbitone readily antagonises all responses of guppies to cunaniol. Cunaniol is highly effective in the release of fry from viviparous fish, due to its effects on neuromuscular function.

The invention is further illustrated by the following examples:

SYNTHETIC EXAMPLES

Example 1

Dried cunani leaves (8 Kg) were hand-crushed and loosely packed into a Q.V.F. extraction vessel which was then filled with petrol 60/80 using a Quickfit glass centrifugal pump and left for one week. The petrol extract (60 liters) was evaporated down to a syrup (190 g) on a climbing film evaporator and subsequently on a water bath.

The Quickfit and Quartz steady state counter current distribution machine (SSDM) was used in the isolation procedure and in the analysis of the crude extracts.

Solvent Preparation

The solvents, methanol (Burroughs A.R. grade) 3,600 mls, Petroleum ether 60/80 (redistilled) 4,000 mls and water (deionised) 400 mls. were mixed in an aspirator (10 1), covered and stirred vigorously for about one hour yielding a syrup (152 g.). This indicates a separation of about 90% of the crude material into upper phase. The portion of the SSDM train represented by tubes $-10$ to $-52$ —constitutes the main fraction of interest. On evaporation to low volume on a water bath, this fraction yielded large quantities of fibrous greenish yellow crystalline material, which has low solubility in water, and a melting point of from 82° to 84° C. When recrystallised from n-hexane the material had a melting point of from 86° to 87° C. Analysis: Calculated for $C_{14}H_{14}O_2$: C78.5, H 6.6%; Found, C 78.77, H 6.41%.

SSDM

The steady state distribution program was based on Counter Current Distribution as described in Technique of Organic Chemistry (Ed. A. Weissberger, 3, Part 1, Publ. Interscience, 149–332 (1956)).

Crude syrup (190 g.) from the cold petrol extraction was dissolved in upper phase solvent (150 mls.). A steady state distribution program was used, based on a Kp value for cunaniol acetate of 0.54 obtained previously from Craig Distribution studies. The mixture was then loaded into the SSDM dosage pump.

The program selecter was set for the sequence $(UL)^3 (U)^3 L(U)^2 (ULUI)^5 (UL)2$. This was derived from a Y/X program of 11 lower phase transferred to 20 upper phase transfers which would retain the cunaniol acetate at tube 0 in the centre of the SSDM train.

The agitation and settle timers were both set at 45 seconds and a feed program of 1 ml./transfer for the duration of 24 transfers, when the feeding program was altered to 0.8 ml./transfer. The feeding program was terminated after 464 transfers and an analysis of the train was made after 620 transfers. Cunaniol acetate was concentrated in the centre of the machine.

It appeared that prolonged heating of petroleum extracts in the initial extraction operations reduced the yield of cunaniol acetate which could best be extracted from the leaves by cold percolation with solvent. The acetate was shown to be easily hydrolysed with sodium bicarbonate.

The upper phase fractions coming out of the machine were discarded. The lower phase fractions coming out of the SSDM were collected in approximately 1 liter fractions. Feeding was stopped after 464 transfers are completed and a further 280 cycles were set to sweep out the machine.

The last lower phase bulk fraction (1 liter) was set aside from the other lower phase fractions which were previously separately collected (5 liters). This lower phase sample was evaporated to an aqueous residue which was then extracted with ether. The ether was removed and the syrup was refluxed with n-hexane (100 ml.) and the supernatant decanted.

A colourless oil was deposited from the n-hexane solution which decomposed to a dark brown oil if left exposed to air and light. This oil exhibited a strong cunaniol-type, 4-banded U.V. spectrum as well as a similar Rf. on T.L.C. and was generally referred to as 'pre-cunaniol oil'. The mass spectrum of this oil indicated the presence of molecular ions of mass 214 with fragments characteristic of cunaniol. A second molecular ion peak at m/e 228 indicated the possibility of cunaniol methyl ether. Further investigation of this oil indicated the presence of cis-cunaniol, which has only about 1/60th of the potency of the trans form but may in some applications be valuable for that reason.

The contents of the train tubes 0 to +30 appearred pale yellow in colour whereas the contents in tubes on the lower bank appeared green in colour. The contents of tubes 0 to +30 and −1 to −52 were evaporated down separately to low bulk, extracted with ether, dried over anhydrous sodium sulphate and concentrated. TLC indicated the presence of cunaniol acetate but no cunaniol.

Purification of cunaniol acetate

A further purification of cunaniol acetate was effected by column chromatography using silica gel eluted with Petrol/benzene. A colourless sample was obtained in a fraction of about 1 liter of benzene which yielded a yellow oil on evaporation. Crystalline cunaniol acetate was easily obtained from ethanol, m.p. 66.5°–67.5° C. Analysis: Calculated for $C_{16}H_{16}O_3$, C 75.0, H 6.3%; Found, C 74.96, H 6.38%.

Column Chromatography of the n-hexane extract

The sample was prepared from the 2nd n-hexane extraction of the lower phase concentrate from the SSDM, the extract being reduced to a syrup which is dissolved in a minimum amount of petrol 60/80.

A column (1 cm×40 cm) fitted with a sinter was packed with silica gel, Merck SG 31 (25 g.) as a slurry in benzene and then equilibrated with the eluting solvent (1% dry enthanol in petrol 60/80). The sample (190 mg.) was put on the column dissolved in petrol (2 ml.) and the elution (flow rate 2 mls./min) was monitored by U.V. (234 mµ.) and optical rotation. An LKB chopper bar multichannel chart recorder was used to plot the changes in U.V., optical rotation and fraction change.

Three main fractions were resolved, after which time a gradient elution was carried out by increasing the concentration of ethanol until the column was stripped with pure ethanol. The second fraction yielded cunaniol which crystallised readily on evaporation of the solvent to low volume.

Some samples appearred to be more strongly adbsorbed on the silica gel and 4% ethanol was required for the elution of the fractions.

However, a separation could be effected in all cases and the second main component from the column appearred to contain cunaniol-type compounds from the U.V. and TLC evidence. Rechromatography of the cunaniol fraction under the same column conditions and monitored on a continuous recording polarimeter indicated two fractions with opposite rotations, the slower running fraction having a positive rotation and the faster running fraction a negative rotation. The latter crystallised from the ethanol-petrol eluate giving a crude m.p. 70°–80° C. and TLC and mass spectrum indicating that cunaniol is the only component.

Isolation of trans-cunaniol

The final purification of trans-cunaniol was best effected by recrystallisation of crude cunaniol material from n-hexane which was then decanted off any residual syrup and left to recrystallise in a refrigerator. In some fractions a colourless oil was deposited before cunaniol crystallised and in some samples no crystalline cunaniol appeared at all, but the cunaniol-type 4 banded U.V. spectrum was still exhibited.

The oily component was referred to as "pre-cunaniol oil". On subsequent analysis these oil fractions were found to yield cunaniol and also two other principal polyacetylenes, hydroxy-tetrahydrocunaniol and contaminating cis-cunaniol.

Purification of a cunaniol containing fraction was achieved by column chromatography using dry benzene on a silica gel column.

Cunaniol crystallised white clusters of fine needles from n-hexane and the solid readily decomposed to a brown material on prolonged exposure to light and air. The pure material possessed a characteristic sickly sweet smell and could be kept for years in the solid state under n-hexane in the dark and in a refrigerator.

Physical properties of trans-cunaniol

Molecular weight 214, $C_{14}H_{14}O_2$. Fine white needles from n-hexane, m.p. 90° C. unstable to oxygen and light.

$[\alpha]_D(0.3, \text{ in CHCl}_3) = -40$

U.V. spectrum: Typical 4 banded $1_{max}$ at 330, 309, 290, 273 nm, mol. absorption coefficient approx 10,000 for each.

Infra-red spectrum: 950 $cm^{-1}$ (trans double bond), 3620 $cm^{-1}$ (hydroxyl), 2220 $cm^{-1}$ (acetylene)

N.M.R. spectrum: d 1.98 ($CH_3$—C≡C—) d6.29, 5.80 (vinyl protons - 16 cps - trans coupling)

Mass spectrum: Leading ion 214. Principle fragments at 71,100, 115 and 143

Properties of cis-cunaniol

Melting point, crystallised from ethanol 100°–102°

[α]D+37.5 (0.3% in chloroform)

I.R. spectrum
  740 $cm^{-1}$ (cis double band, no evidence of trans)
  3600 $cm^{-1}$ (hydroxy)
  2200 $cm^{-1}$ (acetylene)

N.M.R. in deuterochloroform 4.2, 3.9 (vinyl) protons; coupling Jab 10 cycles Jae 8 cycles from spin decoupling experiments; ABX splitting which appears in this region consistent with cis configuration Example 2

The acetyl derivative of cunaniol was prepared in the following manner.

Cunaniol (146 mg) was dissolved in redistilled acetic anhydride (1.5 mls) to which pyridine (5 drops) was added. The reaction mixture was left in the freezing compartment of a refrigerator, under nitrogen and in the dark. Ten days later the reaction mixture was dissolved in ether (25 mls) which gave a yellow solution. The mixture was extracted with 1 N hydrochloric acid (15 mls) in three portions followed by washing with water (10 mls) in two portions. The mixture was then treated with portions of a saturated solution of sodium bicarbonate (10 mls) until there was no effervescence on shaking. The ether was dried over sodium sulphate (2 g) filtered, and evaporated down to a pale yellow syrup (290 mg) on a water bath and under reduced pressure. The syrup was slightly warmed and evacuated by an oil pump connected through a solid $CO_2$/acetone cold trap. The condensate in the cold trap appeared to be acetic acid. The syrup was then extracted with n-hexane (5 mls) to which dry methanol (2 mls) was added and left in a freezing compartment. Large prismatic crystals appeared, which melted, m.p 61°–62° C. to a pale yellow oil with no sign of decomposition.

In another experiment the reaction product, after being dissolved in carbon tetrachloride for N.M.R. measurements, was taken up in a small amount of methanol and white fibrous crystals appeared when placed in the freezer. The fibrous crystals were found to turn voilet on evaporation of the solvent. The crystals melted, m.p. 65.5 –67.50° C., first to a transparent melt with violet coloured fibres embedded in it. The fibres darkened at about 150° C. and darkened the previously transparent melt. The scale-expanded infra red spectrum of the semi-synthetic cunaniol acetate was exactly superimposable on the spectrum obtained from cunaniol acetate isolated from the leaves.

Essential fatty acid esters are prepared by like methods and, generally, derivatision including for example with fatty acid alcohols is by methods known in themselves.

Example 3

Cunaniol was glycosidated. The reagent used in the glycosidation was 2,3,4,6-tetra-O-acetyl-d-glucal, which was prepared from 2,3,4,6-tetra-O-acetyl-d-glucosyl bromide. A method was adopted using the glucal with $BF_3$ as a catalyst to produce the corresponding 2,3-unsaturated glucopyranoside.

D-Glucose (100 g) was used to prepare the acetobromoglucose (186 g), m.p. 85°–86° C. This was converted to the glucal (syrup, 140 g) which crystallised from petrol 60/80 chloroform solvent, m.p. 52°–530° C., [a]$D^{22}$–13.5, C, 2.3 in ethanol.

Cunaniol (120 mgs) was dissolved in sodium dried benzene (10 ml) and boron trifluoride etherate (0.2 mls) was added to the solution which darkened in colour.

Glucal (186 mgs) dissolved in sodium-dried benzene (5 mls) was added dropwise and the mixture left overnight at room temperature. The following day the solution had turned a very dark colour and anhydrous sodium carbonate (approx. 500 mgs) was added and the reaction mixture was filtered.

The benzene solution was added to a column (1×25 m) packed with silica gel, Whatman Chromedia SG31 (30 g) and equilibrated with benzene. A gradient elution was carried out with benzene (sodium dried)/chloroform/ethanol as the eluting solvents. Four well resolved fractions were obtained. The eluate was monitored at 333 mm.

The results are presented in Table I. Approximately 56% reaction occurred with the formation of the glycoside with a trace of the cunaniol acetate formed as a side reaction. The glycosidic fraction was not analysed.

TABLE 1

Column chromatography of cunaniol-glycoside reaction mixture

| Fraction | Eluent | Observation | Yield |
|---|---|---|---|
| 1 | ØH, 200 mls | Colourless cunaniol-type U.V. mol. wt. 256; (cunaniol acetate) | 5 mgs. |
| 2 | ØH, 1 liter | Colourless crystallised on evap$^n$. m.p. 89–90°; (cunaniol) cunaniol-type U.V. | 50 mgs. |
| 3 | $CHCl_3$ | Yellow solution brown syrup on evap$^n$. cunaniol-type U.V. mol. wt. 426; (cunaniol-glycoside) IR: 2220 $cm^{-1}$ (C≡C), 1740 $cm^{-1}$ (ester) | 134 mgs. |
| 4 | ethanol | dark brown solution (discarded) | 10 mgs. |

The glycoside provides a soluble form of cunaniol which is readily liberated on hydrolysis of the glycoside link.

Administration Examples

The compounds may be administered orally, topically, parenterally (subcutaneously, intramuscularly, intravenously), enterally, rectally, vaginally or by any other appropriate route. They may be made up into tablets, hard or soft gel capsules, pastilles, emulsions, enteral or parenteral formulae, foams, ointments, creams, lotions, suppositories, pessaries or any other appropriate form known to those skilled in the art. They may be made up into pharmaceutical dosage forms, or into foods which have a specific medical or health-related purpose.

It will be understood that the absolute quantity of active materials present in any dosage unit should not exceed that appropriate to the rate and manner of administration to be employed but on the other hand should also desirably be adequate to allow the desired rate of administration to be achieved by a small number of doses. The rate of administration will moreover depend on the precise pharmacological action desired. For example, the dosage amounts will be dependent on whether the use is for targeting the whole body or specific tissue (e.g. heart blocking/restarting) or whether the compounds are being used as an analeptic.

The dosage units may suitably be prepared so as to deliver from 1 microg. to 10 g, preferably from 500 microg to 1 g and very preferably from 1 mg to 50 mg of the cunaniol or cunaniol derivative per kg body weight.

The dosage units may contain concentrations of 0.1 microg to 100 mg/ml, preferably 1 microg to 1 mg/ml and very preferably 10 microg to 100 microg/ml of the cunaniol or cunaniol derivative.

When prepared for topical administration or in enteral or parenteral formulations or food they may be made in the formulae containing from 0.01% to 60% by weight of the final formulation, preferably from 0.1% to 30% by weight, and very preferably from 1% to 10% by weight.

The preparations may be used in any disease condition likely to respond to the cunaniol or cunaniol derivative.

I claim:

1. A method of treatment of a person affected by a disease or condition benefited by administration of a reversible heart blocking agent, a neuromuscular active or a neuroactive generally, said neuromuscular active being a drug which acts on myoneural junctions, and said neuroactive being a drug that provides benefits in conditions that affect neurofunction, wherein an effective amount of a cunaniol (2-(1-nonen-3,5,7-triynyl)-3-hydroxytetrahydropyran) of formula I, an anhydrocunaniol of formula II or III or cunanione of formula IV, as set out below, is administered as said agent or active,

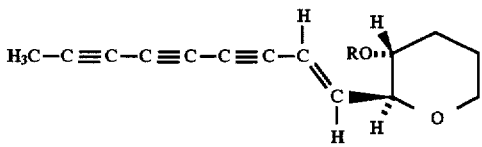

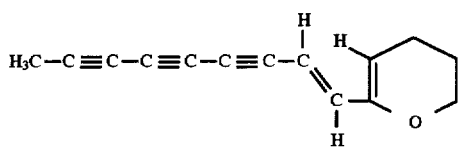

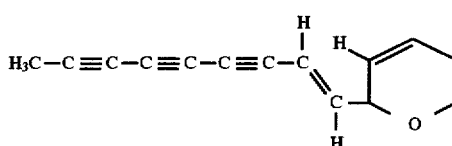

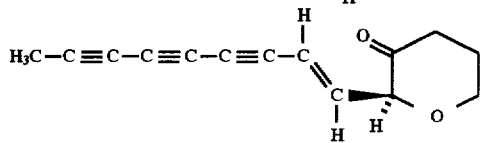

wherein R=H, alkyl, acyl or glycosidyl.

2. The method of treatment according to claim 1, wherein the cunaniol, anhydrocunaniol or cunanione is in the form of a derivative obtained by substitution or hydrogenation or both or by glycosidylation.

3. The method of treatment according to claim 2, wherein the derivative is obtained by substitution at the hydroxy group by etherification with an alkyl or an n-6 or n-3 essential fatty alcohol group.

4. The method of treatment according to claim 3, wherein the alkyl is methyl.

5. The method of treatment according to claim 2, wherein the derivative is obtained by esterification with an acyl.

6. The method of treatment according to claim 5, wherein the acyl is an n-6 or n-3 essential fatty acyl group.

* * * * *